(12) United States Patent
Karlsson et al.

(10) Patent No.: US 9,045,792 B2
(45) Date of Patent: Jun. 2, 2015

(54) IN VITRO METHOD FOR ANALYZING A COMPARISON OF AN INDICATIVE NUMBERIC VALUE TO A PREDETERMINED THRESHOLD SO AS TO ASSESS A LIKELIHOOD OF RISK OR PRESENCE OF ORGAN FAILURE

(75) Inventors: Mathias Karlsson, Karlstad (SE); Sofia Hiort af Ornäs, Trosa (SE)

(73) Assignee: Calmark Sweden AB, Karlstad (SE)

( * ) Notice: Subject to any disclaimer, the term of this patent is extended or adjusted under 35 U.S.C. 154(b) by 0 days.

(21) Appl. No.: 13/822,472

(22) PCT Filed: Sep. 14, 2011

(86) PCT No.: PCT/SE2011/051111
§ 371 (c)(1),
(2), (4) Date: Mar. 18, 2013

(87) PCT Pub. No.: WO2012/036622
PCT Pub. Date: Mar. 22, 2012

(65) Prior Publication Data
US 2013/0171678 A1    Jul. 4, 2013

Related U.S. Application Data

(60) Provisional application No. 61/382,728, filed on Sep. 14, 2010.

(30) Foreign Application Priority Data

Sep. 14, 2010  (SE) ...................................... 1050958

(51) Int. Cl.
| | | |
|---|---|---|
| *C12Q 1/32* | (2006.01) | |
| *A61B 5/145* | (2006.01) | |
| *A61B 5/15* | (2006.01) | |
| *A61B 5/151* | (2006.01) | |
| *G01N 33/573* | (2006.01) | |
| *A61B 5/00* | (2006.01) | |
| *A61B 5/1455* | (2006.01) | |
| *A61B 5/157* | (2006.01) | |
| *G06F 19/24* | (2011.01) | |

(52) U.S. Cl.
CPC .............. *C12Q 1/32* (2013.01); *A61B 5/14546* (2013.01); *A61B 5/14551* (2013.01); *A61B 5/150022* (2013.01); *A61B 5/150343* (2013.01); *A61B 5/150755* (2013.01); *A61B 5/15142* (2013.01); *A61B 5/157* (2013.01); *A61B 2560/0443* (2013.01); *A61B 2562/04* (2013.01); *A61B 2562/06* (2013.01); *G01N 33/573* (2013.01); *G01N 2333/76* (2013.01); *G01N 2800/00* (2013.01); *G06F 19/24* (2013.01); *A61B 5/7275* (2013.01)

(58) Field of Classification Search
USPC .......................................................... 435/26
See application file for complete search history.

(56) References Cited

U.S. PATENT DOCUMENTS

| | | | | |
|---|---|---|---|---|
| 5,639,629 | A  * | 6/1997 | Repine et al. .................... | 435/26 |
| 2008/0213744 | A1* | 9/2008 | Karlsson et al. .................. | 435/2 |
| 2009/0061470 | A1  | 3/2009 | Sauer | |
| 2013/0052675 | A1* | 2/2013 | Karlsson et al. ................ | 435/15 |

FOREIGN PATENT DOCUMENTS

| | | | |
|---|---|---|---|
| WO | WO 2007/041623 | A2 | 4/2007 |
| WO | WO 2008/054303 | A2 | 5/2008 |
| WO | WO 2011/040874 | A1 | 4/2011 |

OTHER PUBLICATIONS

International Searching Authority, Written Opinion mailed Dec. 16, 2011 of corresponding international Application No. PCT/SE2011/051111.

International Searching Authority, International Search Report mailed Dec. 16, 2011 of corresponding international Application No. PCT/SE2011/051111.

Liu, X-S., et al., "A Preliminary Exploration of the Relationship Between Tumour Necrosis Factor (TNF) and Monocytic In Vitro Producation of Interleukin-1 (IL-1) and Internal Organ Dysfunction in Severely Burned Patients", Burns, Jan. 1, 1995, pp. 29-33, vol. 21, No. 21, Elsevier Science Ltd., Great Britian.

Marshall, J. C., et al., "Multiple Organ Dysfunction Score: A Reliable Descriptor of a Complex Clinical Outcome", Critical Care Medicine, Jan. 1, 1995, pp. 1638-1652, vol. 23, No. 10, Williams & Wilkins, USA.

Navarro-Gonzalez, Juan F., et al., "Clinical Implications of Disordered Magnesium Homeostasis in Chronic Renal Failure and Dialysis", Seminars in Dialysis, , Jan.-Feb. 2009, pp. 37-44, vol. 22, No. 1, Wiley Periodicals, Inc., USA.

(Continued)

*Primary Examiner* — Ralph Gitomer
(74) *Attorney, Agent, or Firm* — Alston & Bird LLP

(57) ABSTRACT

The present invention relates to a testing system for analyzing a risk of developing organ failure or presence of organ failure, said system comprising a disposable testing device arranged to receive a biological sample, which testing system is further arranged with means for measuring within said sample the total amount of at least a first biological marker in the form of an intracellular enzyme, and comprising means for analyzing the measured value of said intracellular enzyme, and based on the results thereof being arranged to communicate the risk of developing organ failure or presence of organ failure to an operator of said testing system. The present invention also relates to a method for analyzing a risk of developing organ failure, or analyzing presence of organ failure.

15 Claims, 3 Drawing Sheets

(56) References Cited

OTHER PUBLICATIONS

Rainer, Timothy H., et al., "Derivation of a Prediction Rule for Posttraumatic Organ Failure Using Plasma DNA and Other Variables", Circulating Nucleic Acids in Plasma or Serum II, Sep. 1, 2001, Annals of the New York Academy of Sciences, vol. 945, The New York Academy of Sciences, New York.

Sapin, Vincent, et al., "Rapid Decrease in Plasma D-Lactate as an Early Potential Predictor of Diminished 28-Day Morality in Critically III Septic Shock Patients", Clinical Chemistry and Laboratory Medicine, Jan. 1, 2006, pp. 492-496, vol. 44, No. 4, Walter De Gruyter & Co, Berlin, New York.

Varghese, G. M., et al., "Predictors of Multi-Organ Dysfunction in Heatstroke", Emergency Medicine Journal, Mar. 1, 2005, pp. 185-187, vol. 22, No. 3, Group.bjm.com.

European Patent Office, Extended European Search Report for Application No. 11825536.3, Jan. 22, 2014, 11 pages, Germany.

* cited by examiner

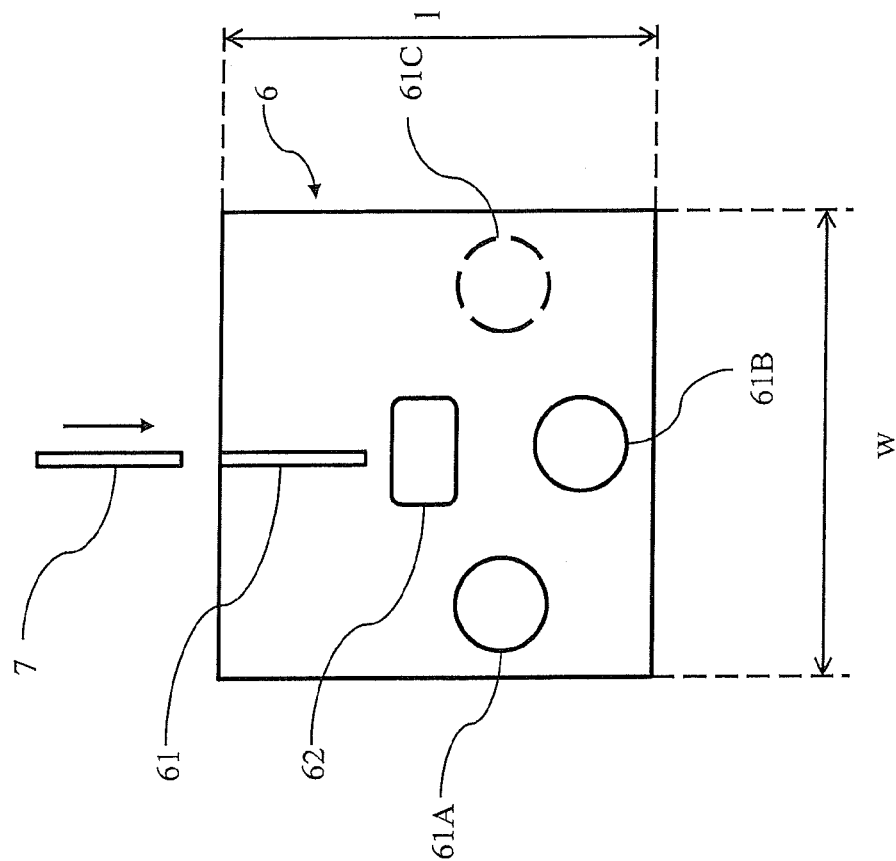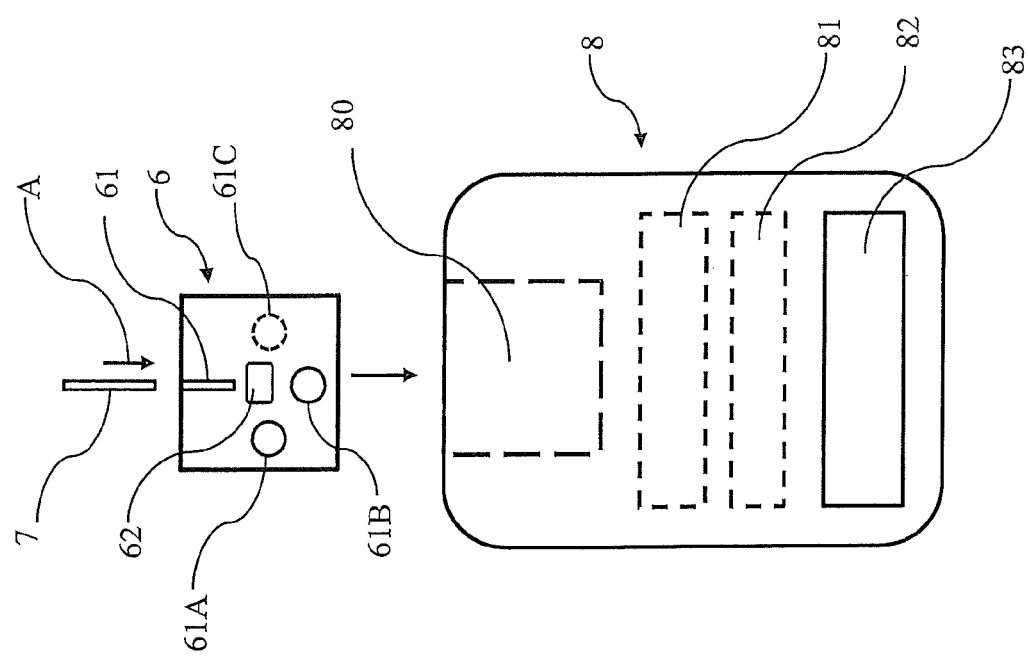

US 9,045,792 B2

IN VITRO METHOD FOR ANALYZING A COMPARISON OF AN INDICATIVE NUMBERIC VALUE TO A PREDETERMINED THRESHOLD SO AS TO ASSESS A LIKELIHOOD OF RISK OR PRESENCE OF ORGAN FAILURE

CROSS REFERENCE TO RELATED APPLICATIONS

This application is a National Stage Application, filed under 35 U.S.C. §371, of International Application No. PCT/SE2011/051111, filed Sep. 14, 2011, which claims priority to U.S. Provisional Application No. 61/382,728, filed Sep. 14, 2010 and Swedish Application No. 1050958-6, filed Sep. 14, 2010, the contents of all of which are hereby incorporated by reference in their entirety.

BACKGROUND OF THE INVENTION

Related Field

The present invention relates to a testing system for analyzing a risk of developing organ failure, or analyzing presence of organ failure. The present invention also relates to a method for analyzing a risk of developing organ failure, or analyzing presence of organ failure.

Description of Related Art

The mortality among intensive care patients is high, and have been so since the last 20 years. The majority of deaths are due to that the patient develops organ failure caused by the original disease or injury. Organ failure may refer to failure in one or more vital organ systems, such as circulation-, renal- and/or respiratory failure. It may also refer to so called multiple organ dysfunction syndrome (MODS), meaning the dysfunction of one or more organ systems, e.g. heart, lungs, kidneys, liver and/or the gastrointestinal tract. The pathophysiology of organ failure (e.g. MODS) is not fully understood, however a crucial factor appears to be the initial ischemia that occurs in the tissue, e.g. as a consequence of shock, which in its turn leads to disrupted micro circulation and the secretion of vasoactive substances such as tromboxane from leucocytes and thrombocytes. Activation of the complementary system is probably one explanation since this damages the endothelium and activates macrophages and polymorphic leucocytes which in their turn leads to the secretion of free radicals and protheolytic enzymes which eventually will lead to cellular death.

One mechanism which plays a part in the course of events related to organ failure (e.g. MODS) and which may lead to cellular death by hypoxia/ischemia is damage of the cellular membrane meaning substances which normally only exist in larger concentrations within the cell leaks out. Examples of such substances are the enzymes lactate dehydrogenase (LDH), aspartate aminotransferase (AST) and alanine aminotransferase (ALT). Clinical studies have also shown a dramatic increase of lactate in the event of hypoxia/ischemia as a result of the anaerobic metabolism that will commence in the tissues. Lactate is presently used as a marker in clinical routines as a measure of tissue perfusion in patients that are critically ill. Lactate is, however, quite an unsatisfactory predictor of organ failure.

Metastudies have shown that the treatments which aim at increasing the transfer of oxygen in critically ill patients only have an effect on survival if the patient has not yet developed organ failure. Therefore it is highly desired that patients who are at risk of developing organ failure receive immediate care and receives adequate treatment.

Other medical studies have been aiming at evaluating whether intracellular enzymes may be used for prognostic purposes. In newborn babies who have been exposed to lack of oxygen during birth LDH, ALT and AST have shown to be very useful in order to predict the risk of developing severe neurological diseases. Also for persons suffering from cancer or patients with severe pneumonia LDH and AST can be valuable for negative prognosis. To date, very little research has been performed regarding the value of enzyme level increase for a general, unselected group of intensive care patients. This is partly due to that adults have an accumulated life history, meaning life style, previous and current diseases and the medical measures that the person has been exposed to such as drugs, treatment, blood transfusions etc. Altogether this complicates the prognostic situation and the predictive value of a certain biomarker, e.g. the intracellular enzyme LDH, is simply not good enough for adults.

For the reasons presented above it would be desired to provide a way to quickly assess the likelihood of developing organ failure, such as MODS, that is applicable to an arbitrary patient, for instance as a part of triage, in order to rapidly being able to deliver proper treatment to patients in need thereof.

BRIEF SUMMARY

It is an object of the present invention to provide the possibility of assessing the likelihood of developing organ failure or the presence of organ failure in a patient which can be performed closely nearby the subject of interest (i.e. the patient) and which can provide for a reliable, quick and easy to perform analysis which enables for rapidly deliver suitable care for patients in urgent need thereof and thereby increasing the chances of survival.

It is to be understood that organ failure may refer to failure of one or more vital organ systems such as the blood circulation system, the renal system and/or the respiratory system. Organ failure may also refer to the dysfunction of one or more vital organs, such as heart, lungs, kidneys, liver and/or the gastrointestinal tract, often called multiple organ dysfunction syndrome (MODS).

It is to be understood that the term "MODS" whenever used hereinafter may be interpreted so as to also include the failure and/or dysfunction of one or more vital organ systems (e.g. blood circulation system, the renal system and/or the respiratory system).

It is also to be understood that in the present description the term "biological marker" refers to a substance, compound or other atom/ion/molecule which is present within a patient and which may reflect or indicate the presence or severity of some physiological state of a patient. In this sense a biological marker may include, without limitation, intracellular enzymes (such as e.g. LDH), albumin, Mg and lactate.

Additional objects of the invention will become evident from the following description and the claims.

The objects of the invention are achieved by a method for analyzing a risk of developing organ failure, or presence of organ failure, said method comprising the providing of a biological sample containing at least one biological marker in the form of an intraceullular enzyme, such as lactate dehydrogenase (LDH), and measuring the total amount of the enzyme (LDH) present in the biological sample.

The objects of the invention are also achieved by a testing system for analyzing a risk of developing organ failure, or analyzing presence of organ failure, said system comprising a disposable testing device arranged to receive a biological sample, said testing system being further arranged to measure within said sample the total amount of at least a first biological marker in the form of an intracellular enzyme, such as lactate dehydrogenase (LDH). The system comprises means for analyzing the acquired measured value, and is arranged to, based on the result thereof, communicate the risk of developing organ failure or presence of organ failure to an operator of said testing system.

The intracellular enzyme LDH is indicative of ongoing cellular damage or that such cellular damage has recently occurred in one or several body tissues. Thus the level of LDH is a suitable factor for determining tissue status and the likelihood of medical conditions associated with cellular damage, such as organ failure. It is possible to also measure other intracellular enzymes instead of LDH, such as aspartate aminotransferase (AST), alanine aminotransferase (ALT) or creatine kinase (CK).

Certain aspects of the invention are described in the context of a method, and it is to be understood that many of those described aspects are also applicable to a testing system and shall therefore be considered to also relate to a testing system according to the invention.

The method and the testing system further comprises measuring the total amount of albumin present in the sample. The reason for determining the amount of albumin in addition to the amount of an intracellular enzyme such as LDH is that in certain situations the levels of LDH may be falsely low, and the determined amount of the enzyme may therefore not always be reliable. This may for instance be the case when the patient to be tested has been exposed to liquid therapy or blood transfusion/s. Therefore, there is a need for correcting possibly falsely-negative data and one quick and easy way of correcting the detected value of LDH is to also assess the amount of albumin in the same sample, as will also later be explained in more detail.

It is to be understood that albumin corresponds to the total amount of albumin present within the sample, however in the present application the term "albumin" is used. It is possible to instead of albumin measure amount of total protein present within the sample.

In the present application "LDH" refers to the total amount of lactate dehydrogenase, not isoenzymes thereof.

Based on the measured amounts of LDH and albumin respectively an indicative numeric value can be calculated, which is compared to a predetermined threshold value whereupon the risk of developing organ failure, or presence of organ failure, can be assessed by determining whether the numeric value exceeds the threshold value or not.

According to one aspect of the invention the risk of developing organ failure or presence of organ failure respectively is assessed by means of the formula:

$$I_1 = (LDH_{tot}/\text{albumin}_{tot}) \quad (1)$$

wherein
$I_1$ is a calculated numeric value indicative of the risk of developing organ failure, or the presence of organ failure,
$LDH_{tot}$ is the total amount of LDH present in the obtained biological sample, and
$\text{albumin}_{tot}$ is the total amount of albumin present in the obtained biological sample.

Thanks to measuring both an intracellular enzyme that may indicate ongoing cellular damage and a plasmaprotein present in the sample, and comparing the two according to the above presented formula (1) it is possible to reveal the "true" status of the patient and thereby reduce the risk of misinterpreting falsely low values of said intracellular enzyme (e.g. LDH). There are various reasons to why detected enzyme levels may be falsely low. Three scenarios leading to such a risk are exemplified as follows: (a) a patient is suffering from capillary leaking of proteins, including LDH and albumin, due to the ongoing pathological process, (b) dilution of the proteins present in plasma including enzymes and albumin due to infusion therapy (e.g. via intravenous route), (c) a decreased protein synthesis due to medical illness could contribute to an inability to respond to poor organ perfusion with a more pronounced increase in LDH. By means of measuring the level of albumin (which is also lowered as a consequence of either of the three scenarios described) and using the result together with the level of the enzyme, the value of $I_1$ will be corrected making it possible to evaluate the patient's physiological status.

In a situation where organ failure can be suspected it is an advantage to be able to assess the present/immediate condition of a patient, which may be done by measuring a biological marker which will become elevated or lowered very quickly depending on how well, or to which extent, the body tissues are perfused. Examples of such biological perfusion indication markers are magnesium and lactate. Thus, according to the invention the amount of such a perfusion indication marker may be measured along with LDH and albumin, and used for assessing the risk or presence of organ failure. According to the present invention the perfusion indication markers correspond to either magnesium or lactate, however it is possible that other substances and biological markers could also be used. Based on the measured amounts of LDH and albumin, and optionally either one of Mg or lactate present in the biological sample, an indicative numeric value is determined which is compared to a predetermined threshold value. The risk of developing organ failure, or presence of organ failure, can thereafter be assessed by determining whether the numeric value exceeds the threshold value or not.

According to one aspect of the invention the risk of developing organ failure or presence of organ failure respectively is assessed by means of either one of the formulas:

$$I_2 = (LDH_{tot}/\text{albumin}_{tot}) * Mg_{tot} \quad (2)$$

or:

$$I_3 = (LDH_{tot}/\text{albumin}_{tot}) * \text{lactate}_{tot}. \quad (3)$$

wherein:
$I_2$ and $I_3$ are calculated indicative numeric values indicating the risk of developing organ failure, or the presence of organ failure,
$LDH_{tot}$ is the total amount of LDH present in the obtained biological sample,
$\text{albumin}_{tot}$ is the total amount of albumin present in the obtained biological sample, and
$Mg_{tot}$ is the total amount of Mg present in the obtained biological sample and $\text{lactate}_{tot}$ is the total amount of lactate present in the obtained biological sample.

The amounts of biological markers LDH, albumin and Mg or lactate respectively can be measured in activity or concentration. LDH is preferably measured in microkatal/L (μkat/L), however it may also be measured in Units/L (U/L). Albumin may be measured in g/L, and Magnesium and lactate in mmol/L. It is however to be understood that various units of measure may be used. If certain units of measure are chosen for the various biological markers of interest a practitioner may perform measurements on samples provided from healthy persons in order to assess an expected threshold of the indicative numeric value $I_1$, $I_2$ or $I_3$ prior to performing analysis for assessing the risk of developing organ failure, or analyzing presence of organ failure.

Said biological sample may be in the form of whole blood, serum or blood plasma. For instance in case the sample corresponds to whole blood a separation device for separating plasma from said whole blood may be used, so that measurement of the respective biological markers is performed in plasma. Evidently several ways of separating plasma from whole blood is conceivable, including equipment such as centrifugation, or by means of filter or membranes.

It is further within the scope of the invention to determine whether the amount of hemoglobin (Hb) in the biological sample (e.g. plasma) exceeds a predetermined level. This is due to that presence of Hb above a predetermined level in a sample is indicative of hemolysis (rupture of red blood cells), and since erythrocytes contains up to 150 times more LDH than blood serum hemolysis is a source of error. Thus in case of presence of Hb above said predetermined level the biological sample needs to be replaced. The amount of Hb may be measured before or simultaneously to measuring biological markers LDH, albumin and lactate or Mg. Many ways of measuring Hb are conceivable, for example colorimetric (change of color of reagents), direct visual detection, spectrophotometric means etc.

By means of simultaneously assessing a triad of biological markers (LDH and albumin plus either one of Mg or lactate) associated with organ failure in the obtained sample and thereupon calculating the value of "I" by means of one of the above shown equations 1)-3), and comparing "I" to a predetermined threshold, an immediate test result can be achieved revealing whether a patient is in danger of acquiring organ failure or not.

According to one aspect of the invention the testing system also comprises data processing means for assessing the risk of developing organ failure, or presence of organ failure, said data processing means being arranged to execute the steps of:
  i. registering the numeric values corresponding to the amounts of $LDH_{tot}$, $Albumin_{tot}$ and optionally either one of $Mg_{tot}$ or lactate tot respectively present in a biological sample,
  ii. analyzing the data obtained in i) by calculating the value of I by means of either one of the formulas (1), (2) or (3),
  iii. attribute a likelihood or risk of the medical condition of organ failure for the patient from which the biological sample was obtained, and
  iv. presenting said likelihood or risk to a medical practitioner operating said testing system.

According to yet another aspect of the invention said parameters total LDH, total albumin and optionally either one of magnesium or lactate present within the sample are assessed/detected simultaneously. This means the test may be performed very quickly and the result achieved in a short time, which is advantageous since it enables for rapidly delivering the correct treatment to the patient thus increasing the chance of survival. According to one aspect of the invention the time from providing a biological sample to assessment of risk of developing organ failure, or assessing presence of organ failure in a patient, is less than 5 minutes, preferably less than 2 minutes. The short time is achievable by means of measuring all biological markers simultaneously, and also by measuring the relevant markers bedside, i.e. as a point of care test, and subsequently make use of either one of the previously presented formulas (1)-(3) for quickly reaching a conclusion regarding the patient's status.

According to yet another aspect of the invention the testing system enables for a point of care testing comprising at least the determination of total LDH in the biological sample. The skilled person understands that by "point of care testing" means a testing that may be run at or near the site of patient care bringing the test conveniently and immediately to the patient, increasing the likelihood that the patient will receive the test results in a timely manner. This is especially advantageous in situations of intensive care where time is crucial and it is vital that the medical status of the patients can be assessed quickly in order to detect whether special care is required. According to yet another aspect of the invention the volume of the sample for point of care detection is from 5 µL-100 µL, more preferred 10 µL-60 µL.

It is also within the scope of the invention that a provided sample may be sent to a standard central laboratory for further evaluation and measurement of the amounts of the biological markers LDH, Albumin and either one of Mg or lactate respectively in order to subsequently assess the risk of organ failure by means of the formula (1), (2) or (3). As is understood by the skilled person the volume of a sample for evaluation in a central lab equals whatever is standard volume requirements for normal laboratory measurement procedures.

The testing method according to the invention may also be very useful in emergency situations where it is beneficial to be able to quickly sort patients according to medical need, i.e. as part of triage. It is understood that the testing method according to the invention may be useful in a number of situations and settings, inter alia for assessment of organ failure in clinical settings, as part of a routine testing protocol or as a laboratory procedure. However a particular advantage associated with the present invention is that testing may be performed in close connection to the patient and give an essentially instant test result on the spot. Thus, it is understood that the testing procedure according to the invention may be used in situations where a central laboratory may not be available like for instance catastrophes, accidents, developing countries and/or in an ambulance. In other situations the usual laboratory routine may take too long time, e.g. in case of suspected sepsis where adequate treatment within one hour result in 80% survival, and every hour of delay increases the mortality by 8%. Also so called MIG (mobile intensive care) teams performing ambulating medical judgments of possible occurrence of organ failure for patients which are treated at ordinary intensive care units would benefit from the testing method and system according to the invention.

According to one aspect of the invention, the testing method further comprises evaluating information regarding a first clinical assessment including the medical history of a patient in the form of test results from blood pressure and body temperature measurements, in order to obtain a fuller picture of the medical condition of the patient.

The present invention further comprises a testing system for assessing a risk of developing organ failure (such as multiple organ dysfunction syndrome), or assessing presence of organ failure in a mammal including human. Said system comprises a disposable testing device for receiving a biological sample, said testing system being arranged to measure within said sample at least the total amount of an intracellular enzyme (such as lactate dehydrogenase (LDH)). According to one aspect the testing system is also arranged to measure within the sample the total amount of albumin, and optionally the total amount of either one of magnesium or lactate. According to one aspect of the testing system the acquired information is further processed in a data processing means comprised by the system arranged to assess the risk of developing organ failure or presence of organ failure in the mammal.

Also comprised by the testing system is means for communicating said risk of developing organ failure or presence of organ failure to an operator of said testing system. According to one embodiment the testing system is preferably small enough to be handheld, and suitable for use in a point of care test.

According to another aspect the testing system comprises measuring means for measuring the biological markers LDH (or other intracellular enzyme), albumin and optionally either one of magnesium or lactate. Said measuring means may be for instance be spectrophotometric equipment or any other conventional known measuring equipment which easily may be combined with a disposable testing device according to the invention, for instance including colorimetric visual detection by using colorimetric reagents.

According to yet another aspect of the invention the provided biological sample originates from a human newborn child. A child has not yet accumulated a medical history in the way an adult has, e.g. due to lifestyle, sicknesses, medications etc. Therefore it is conceivable that intracellular enzyme LDH measured alone is sufficient for predicting risk or presence of organ failure. It is possible to analyze other intracellular enzymes than of LDH, such as aspartate aminotransferase (AST), alanine aminotransferase (ALT) or creatine kinase (CK). Evidently these intracellular enzymes may also be normalized by dividing the total amount thereof with albumin for compensating unknown medical history of a patient.

BRIEF DESCRIPTION OF THE FIGURES

The testing method will hereinafter be described in more detail with reference to the appended drawings. The following descriptions should however be considered as preferred only and are not decisive in a limiting sense.

FIG. 3a shows a schematic planar view of a testing system comprising a disposable testing device and an analyzing instrument according to one example of the invention, and FIG. 3b shows another schematic view of a disposable testing device according to one example of the invention.

DETAILED DESCRIPTION OF VARIOUS EMBODIMENTS

Figure 1:
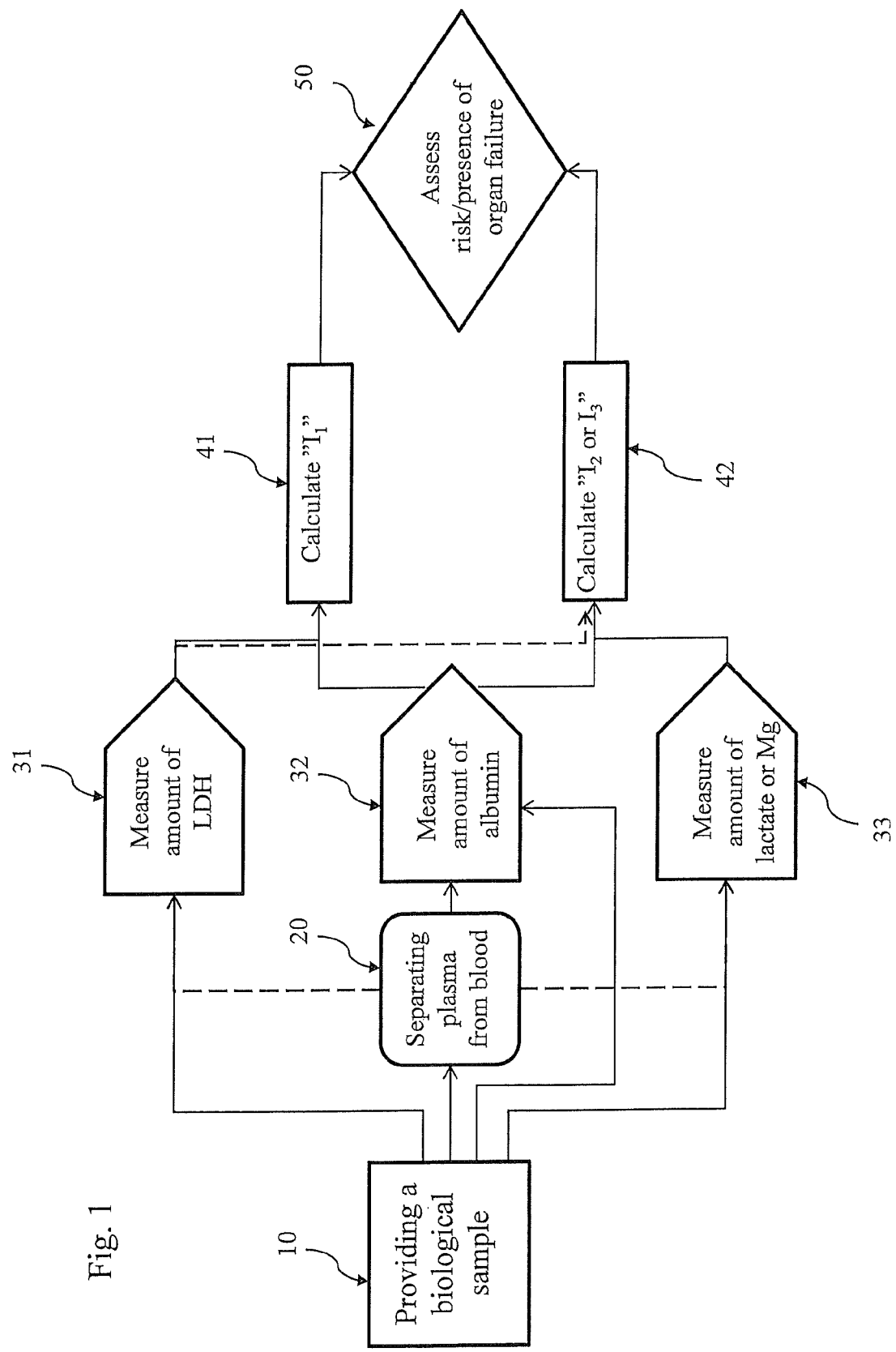
FIG. 1 shows a schematic depiction of the testing method according to one example of the invention.

Referring to FIG. 1 the testing method according to the invention is now to be described in more detail. Herein is seen in a schematic depiction a flowchart illustrating the testing method according to one example of the invention. Firstly a biological sample is provided 10, said sample originating from a mammal, e.g. a human patient. The sample may for instance be in the form of a whole blood sample. In case the sample is a whole blood sample it is preferably brought through some kind of separation device in order to separate plasma from the whole blood 20. A sample of blood may be separated into plasma and blood cells for instance by making the plasma pass through a porous matrix, in this application termed "membrane" on a solid support capable of retaining the blood cells. The plasma is analyzed for biological markers in the form of an intracellular enzyme (e.g. LDH, or some other intracellular enzyme such as aspartate aminotransferase (AST), alanine aminotransferase (ALT) or creatine kinase (CK)) and albumin, and optionally also magnesium or lactate, in any conventional manner. For certain biological markers measurement in plasma is preferred. In such case, if the biological sample is a whole blood sample, it is preferably divided into a portion from which plasma is obtained for the measurement of such markers. For instance lactate may be measured in whole blood whereas LDH, albumin and Mg are preferably measured in plasma. It is within the ambit of the invention to use various known methods for separating whole blood from plasma, such as microcentrifugation, microfluidic compact disc technology and magnetophoresis, for separating plasma from blood cells in the blood sample of the invention.

The sample (e.g. the plasma) is subsequently analyzed with respect to its amount of biomarkers. The amounts of LDH 31 and albumin 32 respectively present within the to sample are measured for all samples. In addition the amount of a perfusion indication marker 33 may optionally be measured, herein in the form of magnesium or lactate, both of which can provide a nearly instant information about changes regarding tissue status, i.e. how well tissue in the body is perfused. However other biological markers which may indicate increased tissue perfusion are also possible to use for analysis. Thus, for each sample there is measured either the amount of magnesium or the amount of lactate 33 present in the sample.

Methods for determination of the activity/concentration of said biological markers include (but are not limited to) colorimetric, spectrophotometric, reflectance photometry, immunochemical, amperometric and biosensor methods.

Said measurements 31, 32, 33 of the respective markers means all the information required to calculate the indicative numeric value $I_1$, $I_2$, $I_3$ has been collected for said sample. Calculation/determination of the indicative value I 41, 42 may be done manually, or preferably by means of some kind of software program. Such a data processing means or software is preferably programmed to gather said information regarding the measured amounts of markers, and calculate the numeric value $I_1$, $I_2$, $I_3$. Such a numeric value $I_1$, $I_2$, $I_3$ is thereafter compared to a predetermined threshold for assessing the risk or presence of organ failure 50. An operator performing the testing method according to the invention may hereby decide whether the patient from whom the sample was obtained needs special medical care, e.g. intensive care, or not.

The threshold value may be determined by evaluating test results from mammals (e.g. humans) that are verified to be healthy, in order to acquire a cut-off value to be used in subsequent real situations. For instance studies have indicated that one possible threshold value is 0.1, meaning an indicative value $I_1$, $I_2$, $I_3$ above 0.1 indicates a risk of organ failure. For the exemplary threshold value of 0.1 the amounts of biological markers LDH, albumin and magnesium respectively were determined using the following units of measure: LDH in microkatal/L; albumin in g/L and Mg in mmol/L. Evidently if other units of measure were to be used, the cut off value of I would change.

Figure 2:
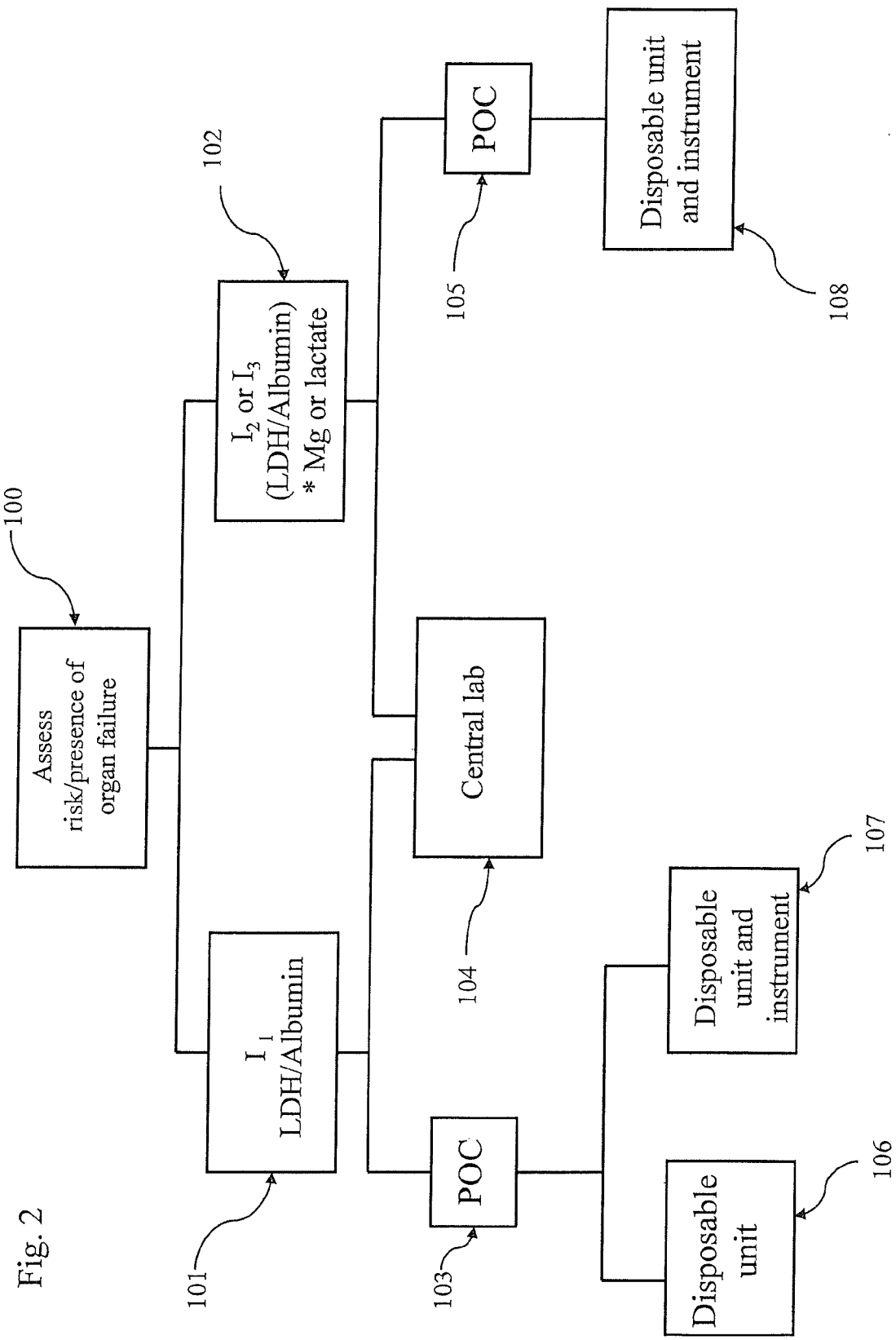
FIG. 2 shows another depiction of possible detection methods according to the invention.

In FIG. 2 there is seen a depiction of the testing method procedures according to one example of the invention. As is illustrated therein, for assessing organ failure 100 two different exemplary alternatives for calculating the indicative numeric value are presented. Either the total amounts of LDH and albumin are measured within the sample, for calculating $I_1$ 101 by means of the equation:

$$I_1 = (LDH_{tot}/\text{albumin}_{tot}) \quad (1)$$

According to another way of calculating the indicative numeric value the total amounts of biological markers LDH, albumin and either one of magnesium and lactate are measured within the sample and $I_2$ or $I_3$ is calculated 102 by means of either one of the equations:

$$I_2 = (LDH_{tot}/\text{albumin}_{tot})*Mg_{tot} \quad (2)$$

or:

$$I_3 = (LDH_{tot}/\text{albumin}_{tot})*\text{lactate}_{tot} \quad (3)$$

In both cases 101, 102 it is evidently possible to transmit the biological sample to a central laboratory 104 for further determination of the values of the biological markers and determine values of $I_1$, $I_2$ and $I_3$ respectively. It is, however, also possible to perform point of care (POC) tests 103, 105 nearby the patient e.g by using a disposable unit 6. Examples of such test instruments and disposable units 6 are further described in FIGS. 3a-3b.

When measuring LDH and albumin, it is possible to provide a disposable unit 106 in the form of a direct detection device intended for independent use and arranged to directly present information regarding the values of the measured biological markers LDH and albumin. Such a solution include, but shall not be limited to, use of chemical reagents for visual detection being integrated within a disposable testing unit, such as a testing card. Another option is to provide a testing system comprising a disposable unit (e.g. in the form of a card 6) and a test instrument 107, wherein such a card is arranged to firstly receive the sample and secondly being inserted into the test instrument where the actual measurements of the biological markers within the sample are performed.

When measuring LDH, albumin and either of magnesium or lactate, a POC test 105 is also possible, but by means of a testing card in combination with an analyzing instrument 108.

Now referring mainly to FIG. 3a, there is seen a schematic view of a testing system according to an exemplary embodiment of the invention, illustrating measurement with a disposable unit 6 and an analyzing instrument 8. Herein said testing system includes a disposable unit 6 in the form of a testing card 6 arranged to receive a liquid biological sample, e.g. via a glass capillary 7 being filled with whole blood. As is indicated with an arrow A the capillary 7 is inserted into the card 6 via a receiving portion 61 and the sample is thereby transferred through a separation device 62, e.g. for separation plasma from the blood cells. The separation device may be a porous matrix (i.e. a filter or membrane). Obviously the sample 7 may be manipulated such that the plasma is separated from the blood cells before it is inserted into the card 6, for instance by centrifugation or any other conventional procedure. After passage through the separation device 62 the sample is transferred into a number of internal detection compartments 61A, 61B, 61C within the card 6. The card is preferably provided with features (as known per se, e.g. micro fluidic channels for distribution of plasma/serum) to allow for plasma from the blood sample to enter from the receiving portion 61 into at least one of the detection compartments 61A, 61B, 61C. In a consecutive step the card 6 is to be placed into a designated portion 80 of the analyzing instrument 80 for measurement of the respective amounts of biomarkers. Analysis may for instance be performed by means of optical instruments 81, i.e. spectrophotometric measurements as known per se. Each of the detection compartments 61A, 61B, 61C within the card 6 can be measured for a selected biological marker (LDH, albumin, Mg and/or lactate). In case the biological sample is in the form of blood or plasma it is also within the ambit of the invention to measure the amount of hemoglobin (Hb) present in said sample to be tested. Measurement of Hb may be done before the sample is introduced into the testing card 6, or detection of Hb may be an integrated part of the testing system per se, e.g. one of the detection compartments being designated for Hb, or by providing a separate visible detection compartment arranged with colorimetric reagents for assessing whether the amount of Hb exceeds a predetermined level indicative of hemolysis. If hemolysis has occurred the biological sample is replaced in order to safeguard that the result of the testing is not altered due to ruptured blood cells.

The results of the measurements (e.g. the amount of biological marker present in the sample) are preferably recorded and gathered by a processor unit 82 integrated within the analyzing instrument 8, which processor preferably also handles the optical equipment and the measurements. One single detection compartment 61A, 61B, 61C can also be used for measuring more than one biomarker, for instance if measuring spectrophotometrically at different wave lengths. The resulting data (i.e. amount of respective biomarkers) is used by the processor unit 82 for calculating said numeric indicative value $I_1$, $I_2$, $I_3$, and preferably also compares said value(s) with a predetermined threshold which threshold is set at a certain level above which organ failure can be suspected or assessed. In order to present the conclusion to an operator as to whether there is a risk or presence of organ failure, said instrument 8 also comprises communication means 83, for instance in the form of a display 83. Evidently the instrument 8 may be a stationary equipment or it may be designed as a smaller, handheld unit suitable for POC testing procedures.

FIG. 3b shows another example of a testing system according to the invention, here including merely a disposable card 6 intended for POC tests and quick assessment of the risk of developing organ failure, or presence of organ failure in a mammal including human, beneficially a compact and handheld unit which is user friendly and very intuitive in order to simplify the assessment procedure. As in the example shown in FIG. 3a, the disposable card 6 comprises a portion 61 for receiving a glass capillary 7 carrying a liquid biological sample such as whole blood or plasma. As is obvious to the skilled person, other methods for providing a sample apart from a capillary device 7 are conceivable. The sample is arranged to be transferred through a separation device 62 integrated with the card 6, and further entering the at least two visible detection compartments 61A, 61B: one for detecting LDH and one for detecting albumin. The card 6 can be provided with more than two visible detection compartments 61A, 61B, 61C if more than two biological markers are to be measured. Each detection compartment 61A, 61B, 61C is arranged with predeposited chemical reagents which will change color upon contact with a biological marker to be measured. Hereby, determination of the amount of biological marker present within a sample can be performed by means of colorimetric analysis, meaning direct visual detection is possible. The card 6 may be modified so that certain color combinations equal "risk"/"no risk" of developing organ failure. Different methods for achieving this are conceivable, such as a given color combination being indicative of a physiological state, e.g. high level (e.g. above a predetermined cut-off level) of LDH in combination with a low value of albumin is indicative of organ failure.

The disposable unit 6 according to the embodiment in FIG. 3b can be handheld and has a length 1 between 3-15 cm, preferably 5-10 cm, and a width w between 0.5-5 cm, preferably 2-4 cm, and a thickness (not shown) between 0.1-3 cm, preferably 0.3-0.7 cm.

The testing method and the testing system according to the invention is further clarified by the following non-limiting examples:

EXAMPLES

Example 1

A seventy-five year old woman with known malignancy and cardio-vascular disease was admitted to emergency rescue (ER) for third time during the last ten days due to abdominal pain. The woman develops MODS during the coming 24h due to hypovolemic shock as a result of gastro intestinal bleeding. LDH is only slightly increased (3.7 microkatal/L) but low albumin (16 g/L) and increased Mg (1.1 mmol/L) gives a high indicative value $I_2$ of 0.25 and calls for immediate medical care.

Example 2

A healthy man acquires chest pain at home. LDH is assessed at admittance 16.9 mikrokatal/L, Albumin 19 g/L and Mg 1.12 mmol/L. This means all included variables are abnormal and $I_2$ is highly increased to 0.996. The man later develops organ failure including circulatory failure as a result of myocardial infarction.

Example 3

A seventy-three year old woman is newly treated surgically for colorectal tumor. Afterwards she develops fever and abdominal pain. $I_2$ is low (0.09) with LDH 2.9 mikrokatal/L, Albumin of 32 g/L and Mg 1.0 mmol/L. The woman is treated with fluids at the intensive care unit for 24 h. No failure of vital organ system occurs.

The skilled person realizes that a large variety of modifications may be performed without the use of inventive skill, departing from the description above, e.g. use of some other known detection method for measuring biological markers than herein described. It is therefore to be understood that the invention is not limited to the specific embodiments and examples disclosed and that modifications and other embodiments are intended to be included within the scope of the appended claims.

The invention claimed is:

1. An in- vitro method for analyzing a risk of developing organ failure or presence of organ failure, said method comprising the steps of:
   a) providing a biological sample,
   b) measuring the total amount of lactate dehydrogenase (LDH) present in the biological sample,
   c) measuring the total amount of albumin present within the provided sample,
   d) calculating an indicative numeric value (Ii) based on a relationship between the results obtained from steps (b) and (c), wherein the indicative numeric value (Ii) is calculated based upon a formula where Ii=(LDHtot/albumintot),
   e) comparing the calculated indicative numeric value (Ii) to a predetermined threshold, and
   f) analyzing the result of the comparison made in e) so as to assess the risk of developing organ failure or presence of organ failure.

2. The method of claim 1, wherein the risk of developing organ failure, or presence of organ failure, is assessed by means of the formula:

Ii=(LDHtot/albumintot)

wherein:
   Ii is a calculated numeric value indicative of the risk of developing organ failure, or the presence of organ failure,
   LDHtot is the total amount of LDH present in the provided biological sample, and
   albumintot is the total amount of albumin present in the provided biological sample.

3. The method according to claim 1 which in connection to either of step b) or c), further comprises measuring the total amount of a biological perfusion indication marker present within the sample, and based on the result from b)-d) calculating an indicative numeric value (I2) indicative of the risk of developing organ failure, or the presence of organ failure, wherein said indicative numeric value (I2) is assessed by means of the formula: I2 =(LDHtot/albumintot)*(biological marker)tot.

4. The method of claim 3, wherein the biological perfusion indication marker is at least one of magnesium (Mg) and lactate.

5. The testing method of claim 3, wherein the risk of developing organ failure, or presence of organ failure, is assessed by means of the formula:

h,3=(LDHtot/albumin^)*(biological marker)tot wherein:
   h,3 is a calculated numeric value indicative of the risk of developing organ failure, or the presence of organ failure,
   LDHtot is the total amount of LDH present in the obtained biological sample,
   albumin^ is the total amount of albumin present in the obtained biological sample, and
   (biological marker)tot is the total amount of a biological perfusion indication marker present in the obtained biological sample.

6. The method of claim 3, wherein at least two of said biomarkers total LDH, total albumin, magnesium, and lactate measured in steps b)-c) are measured simultaneously.

7. The method of claim 1, wherein the biological sample is a blood sample.

8. The method of claim 1, wherein the volume of the biological sample is from 50 μL, -150 μL.

9. The method of claim 8, wherein the volume of the biological sample is from 10-60 μL.

10. The method of claim 1, wherein said method is a point of care testing method.

11. The method of claim 1, wherein said measuring of total LDH total albumin and total amount of biological perfusion indication marker respectively comprises detecting with spectrophotometric means.

12. The method of claim 1, wherein the time from providing a biological sample to assessment of risk of developing organ failure, or assessing presence of organ failure, is less than 5 minutes.

13. The method of claim 1, wherein the time from providing a biological sample to assessment of risk of developing organ failure, or assessing presence of organ failure, is less than 2 minutes.

14. The method according to claim 1, for use in a triage situation.

15. The method according to claim 1, further comprising additional test results from blood pressure and body temperature measurement.

* * * * *

UNITED STATES PATENT AND TRADEMARK OFFICE
CERTIFICATE OF CORRECTION

PATENT NO. : 9,045,792 B2
APPLICATION NO. : 13/822472
DATED : June 2, 2015
INVENTOR(S) : Karlsson et al.

Page 1 of 1

It is certified that error appears in the above-identified patent and that said Letters Patent is hereby corrected as shown below:

Title Page

"(54)  IN VITRO METHOD FOR ANALYZING A COMPARISON OF AN INDICATIVE NUMBERIC VALUE TO A PREDETERMINED THRESHOLD SO AS TO ASSESS A LIKELIHOOD OF RISK OR PRESENCE OF ORGAN FAILURE"

should read

--(54)  AN IN VITRO METHOD FOR ANALYZING A COMPARISON OF AN INDICATIVE NUMERIC VALUE TO A PREDETERMINED THRESHOLD SO AS TO ASSESS A LIKELIHOOD OF RISK OR PRESENCE OF ORGAN FAILURE--

Signed and Sealed this
Twenty-seventh Day of October, 2015

Michelle K. Lee
*Director of the United States Patent and Trademark Office*